United States Patent
Li et al.

(10) Patent No.: US 9,928,617 B2
(45) Date of Patent: Mar. 27, 2018

(54) SYSTEM AND METHOD FOR MULTI-MODALITY TIME-OF-FLIGHT ATTENUATION CORRECTION

(71) Applicant: THE GENERAL HOSPITAL CORPORATION, Boston, MA (US)

(72) Inventors: Quanzheng Li, Cambridge, MA (US); Georges El Fakhri, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 283 days.

(21) Appl. No.: 14/440,981

(22) PCT Filed: Mar. 14, 2013

(86) PCT No.: PCT/US2013/031397
§ 371 (c)(1),
(2) Date: May 6, 2015

(87) PCT Pub. No.: WO2014/074148
PCT Pub. Date: May 15, 2014

(65) Prior Publication Data
US 2015/0262389 A1 Sep. 17, 2015

Related U.S. Application Data

(60) Provisional application No. 61/724,159, filed on Nov. 8, 2012.

(51) Int. Cl.
*G06K 9/00* (2006.01)
*G06T 11/00* (2006.01)
*A61B 5/055* (2006.01)
*G01T 1/16* (2006.01)

(52) U.S. Cl.
CPC ............ *G06T 11/005* (2013.01); *A61B 5/055* (2013.01); *G01T 1/1603* (2013.01)

(58) Field of Classification Search
None
See application file for complete search history.

(56) References Cited

U.S. PATENT DOCUMENTS

| | | | |
|---|---|---|---|
| 8,600,136 B2 * | 12/2013 | Schweizer | G01R 33/481 382/131 |
| 9,213,074 B2 * | 12/2015 | van der Kouwe | G01R 33/482 |
| 2010/0021034 A1 | 1/2010 | Lenglet et al. | |

(Continued)

FOREIGN PATENT DOCUMENTS

WO WO 2010032168 A2 * 3/2010 ............ G01R 33/481

OTHER PUBLICATIONS

International Search Report dated Aug. 22, 2013, in connection with PCT/US2013/031397.

*Primary Examiner* — Vu Le
*Assistant Examiner* — Samah Beg
(74) *Attorney, Agent, or Firm* — Quarles & Brady LP (57) ABSTRACT

A system and method for determining, from registered positron emission tomography (PET) sinogram data and magnetic resonance (MR) image data, an estimated attenuation sinogram uses a data consistency condition to evaluate a gradient of the PET sinogram data using the MR image data. An image of the subject is reconstructed using the estimate attenuation sinogram.

13 Claims, 5 Drawing Sheets

(56) References Cited

U.S. PATENT DOCUMENTS

| | | | |
|---|---|---|---|
| 2011/0015904 A1* | 1/2011 | Fenchel | A61B 6/037 703/2 |
| 2011/0103669 A1* | 5/2011 | Michel | G06T 11/005 382/131 |
| 2011/0309251 A1* | 12/2011 | Fenchel | A61B 6/037 250/362 |
| 2012/0259196 A1 | 10/2012 | Tanaka et al. | |
| 2013/0101193 A1* | 4/2013 | Ra | G06T 11/005 382/131 |
| 2013/0322715 A1* | 12/2013 | Wollenweber | A61B 5/055 382/131 |
| 2014/0056500 A1* | 2/2014 | Bal | G06T 11/005 382/131 |
| 2014/0099009 A1* | 4/2014 | Lonn | G06T 11/005 382/131 |
| 2014/0119630 A1* | 5/2014 | Sowards-Emmerd | A61B 6/032 382/131 |
| 2014/0334702 A1* | 11/2014 | El Fakhri | G06T 11/005 382/131 |
| 2015/0057535 A1* | 2/2015 | Sitek | A61B 6/5205 600/426 |
| 2015/0117733 A1* | 4/2015 | Manjeshwar | G06T 11/003 382/131 |
| 2015/0193927 A1* | 7/2015 | Wang | G01T 1/1647 382/131 |
| 2016/0073993 A1* | 3/2016 | Ouyang | A61B 5/721 600/411 |
| 2017/0061629 A1* | 3/2017 | Zhu | G06T 5/007 |

\* cited by examiner

SYSTEM AND METHOD FOR MULTI-MODALITY TIME-OF-FLIGHT ATTENUATION CORRECTION

CROSS-REFERENCE TO RELATED APPLICATIONS

This application represents the national stage entry of PCT International Application No. PCT/US2013/031397 filed Mar. 14, 2013, which claims priority to U.S. Provisional Application Ser. No. 61/724,159, filed Nov. 8, 2012, the disclosures of which are incorporated by reference here in their entirety for all purposes.

STATEMENT REGARDING FEDERALLY SPONSORED RESEARCH

This invention was made with government support under Grant Numbers CA165221, EB013293 awarded by the National Institutes of Health. The government has certain rights in the invention.

BACKGROUND OF THE INVENTION

The field of the invention is multi-modality imaging systems and methods, such as positron emission tomography (PET) and magnetic resonance imaging systems and methods. More particularly, the present invention relates to improved time-of-flight PET/MR imaging systems and methods.

Positrons are positively charged electrons which are emitted by radionuclides that have been prepared using a cyclotron or other device. These are employed as radioactive tracers called "radiopharmaceuticals" by incorporating them into substances, such as glucose or carbon dioxide. The radiopharmaceuticals are administered to a patient and become involved in biochemical or physiological processes such as blood flow; fatty acid and glucose metabolism; and protein synthesis.

As the radionuclides decay, they emit positrons. The positrons travel a very short distance before they encounter an electron, and when this occurs, they are annihilated and converted into two photons, or gamma rays. This annihilation event is characterized by two features which are pertinent to PET scanners—each gamma ray has an energy of 511 keV and the two gamma rays are directed in nearly opposite directions. An image indicative of the tissue concentration of the positron emitting radionuclide is created by determining the number of such annihilation events at each location within the field of view.

The PET scanner includes one or more rings of detectors which encircle the patient and which convert the energy of each 511 keV photon into a flash of light that is sensed by a photomultiplier tube (PMT). Coincidence detection circuits connect to the detectors and record only those photons which are detected simultaneously by two detectors located on opposite sides of the patient. The number of such simultaneous events indicates the number of positron annihilations that occurred along a line joining the two opposing detectors. Within a few minutes hundreds of million of events are recorded to indicate the number of annihilations along lines joining pairs of detectors in the ring. These numbers are employed to reconstruct an image using well known computed tomography techniques.

Positron emission tomography provides quantitative images depicting the concentration of the positron emitting substance throughout the patient. The accuracy of this quantitative measurement depends in part on the accuracy of an attenuation correction that accounts for the absorption of some of the gamma rays as they pass through the patient. The attenuation correction factors modify the sinogram which contains the number of annihilation events at each location within the field of view. There are a number of methods used to measure, or calculate the attenuation factors. These include calculating the attenuation correction; measuring attenuation correction; and a hybrid, or segmented tissue technique. In this regard, attenuation correction is essential for the quantitation of PET data. However, as described above, this can be difficult to achieve with a PET system. There are several methods proposed to estimate attenuation correction from emission PET data; however, each has shortcomings.

As such, it has been recently proposed by M. Defrise, A. Rezaei, and J. Nuyts, "Time-of-flight PET data determine the attenuation sinogram up to a constant," Phys. Med. Biol., vol. 57, no. 4, pp. 885, 2012, that an attenuation sinogram that can be uniquely reconstructed from ideal time-of-flight (TOF) PET emission data by estimating the gradient of an attenuation sinogram using a TOF PET data consistency condition. Defrise et al. propose a two-step method to compute attenuation correction; however, the method suffers from unstable estimations of high frequency components and also areas with low photo counts, even without the presence of Poisson noise.

Accordingly, there is a need for a robust system and method for determining attenuation correction in PET imaging.

SUMMARY OF THE INVENTION

The present invention overcomes the aforementioned drawback by providing a system and method for using anatomical information, such as automatically or manually co-registered magnetic resonance (MR) images, co-registered with PET data, to provide an improved maximum a posteriori (MAP) TOF PET attenuation-estimation framework incorporating anatomical information into the framework. Gradient estimation and integration can be used to formulate a data fitting term, and joint entropy between feature vectors extracted from an anatomical sinogram (forward projection of the anatomical image) and attenuation sinogram can be used as a prior term.

In accordance with one aspect of the disclosure, a method for correcting attenuation of a positron emission tomography (PET) image using magnetic resonance (MR) imaging data includes acquiring PET sinogram data of a subject and acquiring MR image data of the subject that is registered with respect to the PET sinogram data. The method also includes producing, using the PET sinogram data and MR image data, an estimate attenuation sinogram using a data consistency condition and joint entropy based prior. The method further includes reconstructing a PET image using the estimated attenuation sinogram.

In accordance with another aspect of the disclosure, a system includes a non-transitive storage medium having stored thereon positron emission tomography (PET) sinogram data of a subject and magnetic resonance (MR) image data of the subject that is registered with respect to the PET sinogram data. The system also includes a processor configured to access the non-transitive storage medium and determine therefrom an estimate attenuation sinogram using a data consistency condition to evaluate a gradient of the PET sinogram data using the MR image data. The processor is also configured to reconstruct an image of the subject using the estimate attenuation sinogram.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DESCRIPTION OF THE PREFERRED EMBODIMENT

Figure 1:
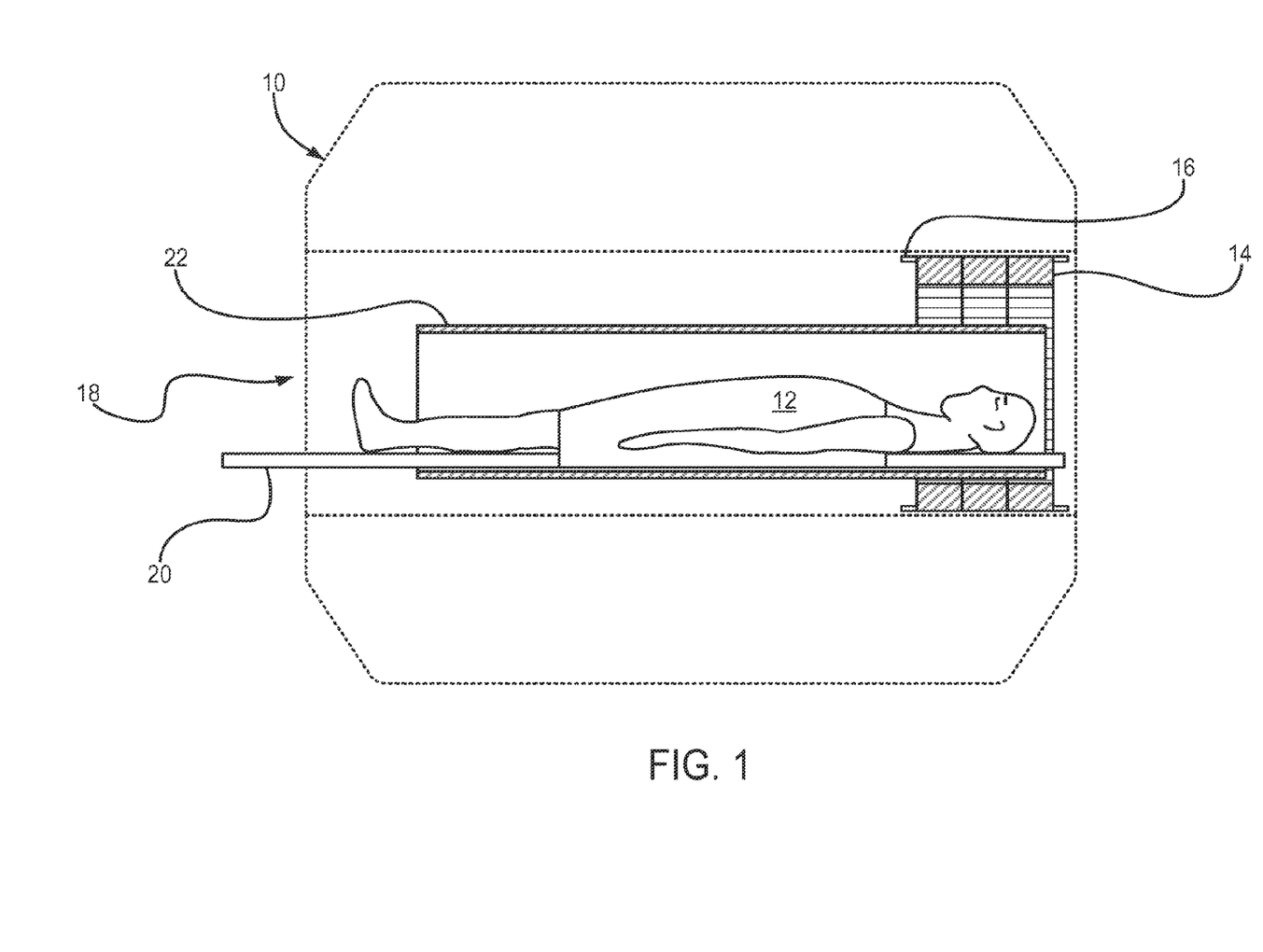
FIG. 1 is a pictorial view with parts cut away of a combination PET scanner system and MRI system in accordance with the present invention.

Referring to FIG. 1, the present disclosure may be used with an MRI system having a cylindrical magnet assembly 10 that receives a subject 12 to be imaged. Disposed within the magnet assembly 10 is a plurality of PET detector rings 14 that are supported by a cylindrical PET gantry 16. Accordingly, each detector ring 14 has an outer diameter dimensioned to be received within a bore 18 of the magnet assembly 10. In an alternate embodiment, a single PET detector ring may be utilized. A patient table 20 is provided to receive a patient to be imaged. The gantry 16 is slidably mounted on the patient table 20 such that its position can be adjusted within the magnet assembly 10 by sliding it along the patient table 20. An RF coil 22 is employed to acquire MR signal data from a patient and is positioned between the PET detector rings 14 and the subject 12 to be imaged. PET and MR data acquisitions are carried out on the subject 12, either simultaneously, in an interlaced or interleaved manner, or sequentially. Combination PET/MR imaging systems have been described, for example, in U.S. Pat. No. 7,218,112 and in U.S. Patent Application No. 2007/0102641, which are incorporated herein by reference in their entirety. Additionally, other combination PET/MR imaging systems variations can be appreciated, such as those in which the PET and MRI systems are physically adjacent, but not fully incorporated within each other.

The MRI magnet assembly 10 is connected to an MRI system that will be described in detail with respect to FIG. 3. The detector rings 14 are connected to a PET system that will be described in detail with respect to FIG. 2.

Figure 2:
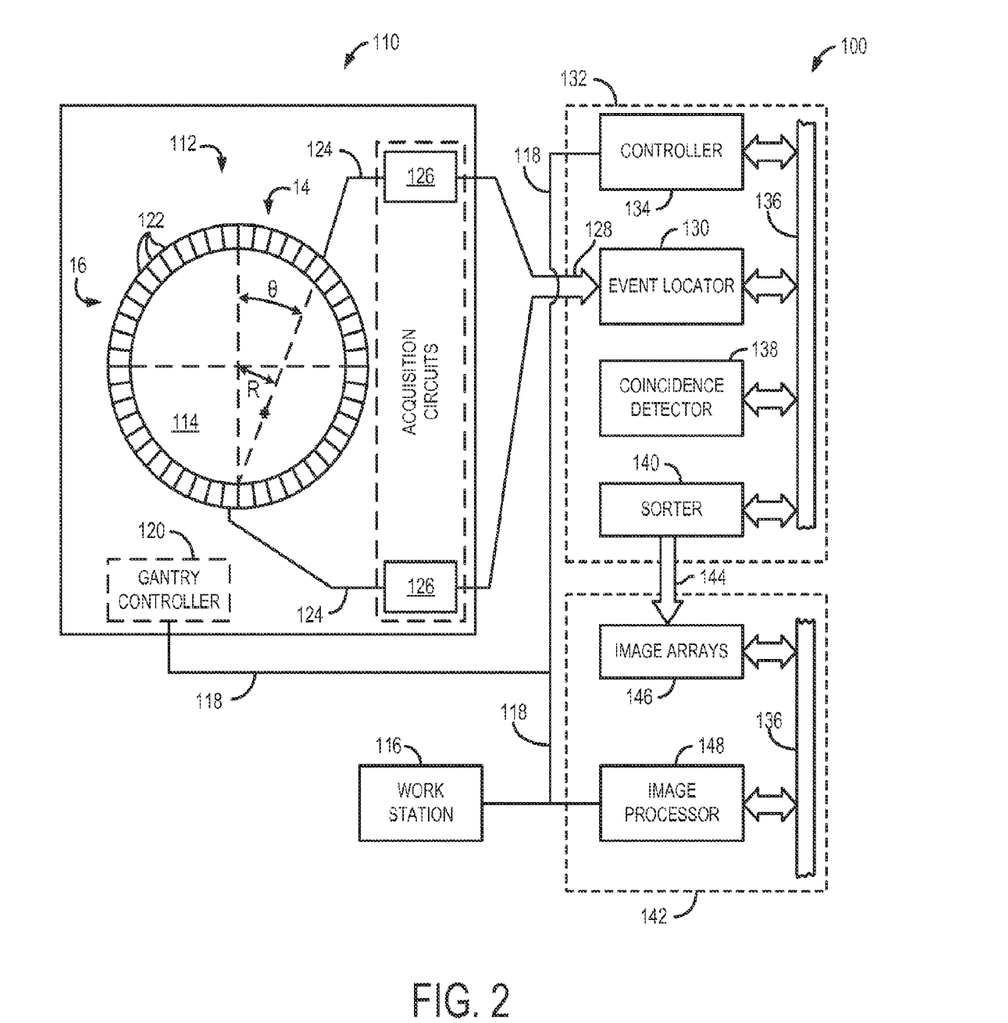
FIG. 2 is a schematic diagram of the PET scanner portion of the system of FIG. 1.

Specifically, referring to FIG. 2, the hardware 100 of the PET system for use with the present invention is illustrated. The PET system includes an imaging hardware system 110 that includes a detector ring assembly 112, that includes the above-described PET detector rings 14 arranged about a central axis, or bore 114, to form the PET gantry 16. An operator work station 116 communicates through a communications link 118 with a gantry controller 120 to control operation of the imaging hardware system 110.

The detector ring assembly 112 is formed of a multitude of radiation block detector units 122. Each radiation block detector unit 122 includes a set of scintillator crystals that is disposed in front of an array of photomultiplier tubes or a position-sensitive photomultiplier tube (not shown). Each photomultiplier tube produces a signal responsive to detection of a photon on communications line 124 when a scintillation event occurs. A set of acquisition circuits 126 receive the signals and produce signals indicating the event coordinates (x, y) and the total energy associated with the photons that caused the scintillation event. These signals are sent through a cable 128 to an event locator circuit 130. Each acquisition circuit 126 also obtains information from the detector's signals that indicates the exact moment the scintillation event took place. For example, sophisticated digital electronics can obtain this information regarding the precise instant in which the scintillations occurred from the samples of the signals used to obtain energy and event coordinates.

The event locator circuits 130 in some implementations, form part of a data acquisition processing system 132 that processes the signals produced by the acquisition circuits 126. The data acquisition processing system 132 usually includes a general controller 134 that controls communications for example, by way of a backplane bus 136, and on the general communications network 118. The event locator circuits 130 assemble the information regarding each valid event into a set of numbers that indicate precisely when the event took place, the position in which the event was detected, and the energy deposited by the photon. This event data packet is conveyed to a coincidence detector 138 that is also part of the data acquisition processing system 132.

The coincidence detector 138 accepts the event data packets from the event locator circuit 130 and determines if any two of them are in coincidence. Coincidence data is provided to a sorter 140. The function of the sorter in many traditional PET imaging systems is to receive the coincidence data packets and generate memory addresses from the coincidence data packets for the efficient storage of the coincidence data. In that context, the set of all projection rays, or lines of response, that point in the same direction (θ) and pass through the scanner's field of view (FOV) is a complete projection, or "view". The distance (R) between a particular line of response and the center of the FOV locates that line of response within the FOV. The sorter 140 counts all of the events that occur on a given line of response (R, θ) during the scan by sorting out the coincidence data packets that indicate an event at the two detectors lying on this line of response. Once all events are counted, the coincidence counts are organized, for example, as a set of two-dimensional arrays, one for each axial image plane, and each having as one of its dimensions the projection angle θ and the other dimension the distance R. This θ by R map of the measured events is call a histogram or, more commonly, a sinogram array. It is these sinograms that are processed to reconstruct images that indicate the number of events that took place at each image pixel location during the scan. The sorter 140 counts all events occurring along each line of response (R, θ) and organizes them into an image data array.

The sorter 140 provides the image dataset array to an image processing/reconstruction system, for example, by way of a communications link 144 to be stored in an image array 146. The image array 146 holds the dataset array for access by an image processor 148 that reconstructs one or more images corresponding to the dataset array.

Figure 3:
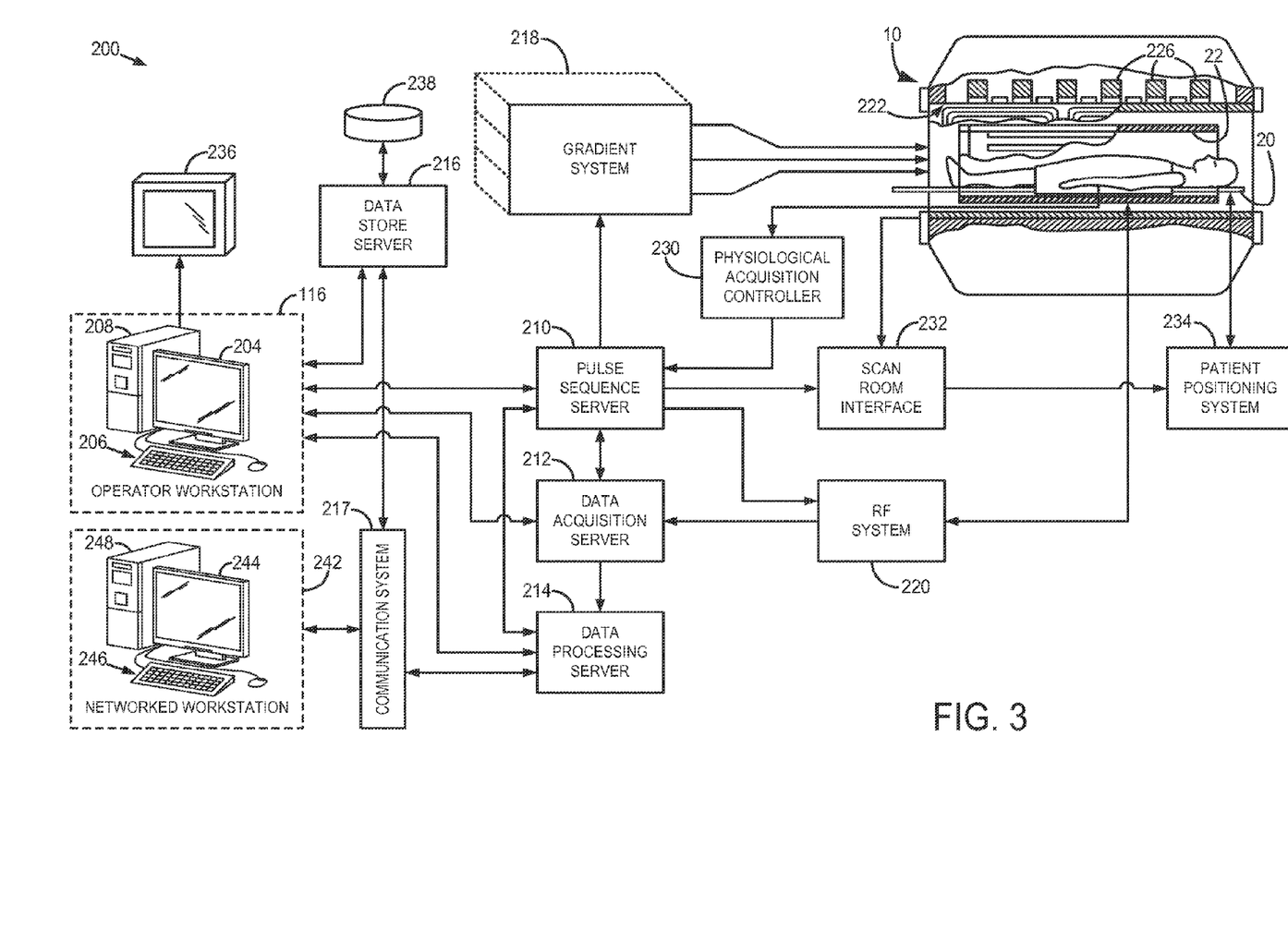
FIG. 3 is a schematic diagram of the MRI system portion of the system of FIG. 1.

Referring particularly now to FIG. 3, an example of hardware for the MRI system is illustrated. The MRI system hardware 200 is likewise connected to the operator workstation 116, which, as illustrated, will typically includes a display 204, one or more input devices 206, such as a keyboard and mouse, and a processor 208. From the perspective of the MR hardware 200, the operator workstation 116 communicates with four servers: a pulse sequence server 210; a data acquisition server 212; a data processing server 214; and a data store server 216. The operator workstation 116 and each server 210, 212, 214, and 216 are connected to communicate with each other. For example, the servers 210, 212, 214, and 216 may be connected via a communication system 217, which may include any suitable network connection, whether wired, wireless, or a combination of both. As an example, the communication system 217 may include both proprietary or dedicated networks, as well as open networks, such as the internet.

The pulse sequence server 210 functions in response to instructions downloaded from the operator workstation 116 to operate a gradient system 218 and the RF system 220. Gradient waveforms necessary to perform the prescribed scan are produced and applied to the gradient system 218, which excites gradient coils in an assembly 222 to produce the magnetic field gradients $G_x$, $G_y$, and $G_z$ used for position encoding magnetic resonance signals. The gradient coil assembly 222 forms part of the above-described magnet assembly 10 that includes a polarizing magnet 226 and The RF coil 22, which may be a whole-body or local coil (not shown).

RF waveforms are applied by the RF system 220 to the RF coil 22, or a separate local coil, in order to perform the prescribed magnetic resonance pulse sequence. Responsive magnetic resonance signals detected by the RF coil 22, or a separate local coil, are received by the RF system 220, where they are amplified, demodulated, filtered, and digitized under direction of commands produced by the pulse sequence server 210. The RF system 220 includes an RF transmitter for producing a wide variety of RF pulses used in MRI pulse sequences. The RF transmitter is responsive to the scan prescription and direction from the pulse sequence server 210 to produce RF pulses of the desired frequency, phase, and pulse amplitude waveform. The generated RF pulses may be applied to the whole-body RF coil 22 or to one or more local coils or coil arrays.

The RF system 220 also includes one or more RF receiver channels. Each RF receiver channel includes an RF preamplifier that amplifies the magnetic resonance signal received by the RF coil 22 to which it is connected, and a detector that detects and digitizes the I and Q quadrature components of the received magnetic resonance signal. The magnitude of the received magnetic resonance signal may, therefore, be determined at any sampled point by the square root of the sum of the squares of the and components:

$$M=\sqrt{I^2+Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 210 also optionally receives patient data from a physiological acquisition controller 230. By way of example, the physiological acquisition controller 230 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 210 to synchronize, or "gate," the performance of the scan with the subject's heart beat or respiration.

The pulse sequence server 210 also connects to a scan room interface circuit 232 that receives signals from various sensors associated with the condition of the patient and the magnet system. It is also through the scan room interface circuit 232 that a patient positioning system 234 receives commands to move the patient table 20 to desired positions during the scan.

The digitized magnetic resonance signal samples produced by the RF system 220 are received by the data acquisition server 212. The data acquisition server 212 operates in response to instructions downloaded from the operator workstation 116 to receive the real-time magnetic resonance data and provide buffer storage, such that no data is lost by data overrun. In some scans, the data acquisition server 212 does little more than pass the acquired magnetic resonance data to the data processor server 214. However, in scans that require information derived from acquired magnetic resonance data to control the further performance of the scan, the data acquisition server 212 is programmed to produce such information and convey it to the pulse sequence server 210. For example, during prescans, magnetic resonance data is acquired and used to calibrate the pulse sequence performed by the pulse sequence server 210. As another example, navigator signals may be acquired and used to adjust the operating parameters of the RF system 220 or the gradient system 218, or to control the view order in which k-space is sampled.

The data processing server 214 receives magnetic resonance data from the data acquisition server 212 and processes it in accordance with instructions downloaded from the operator workstation 116. Images reconstructed by the data processing server 214 may be conveyed back to the operator workstation 116. Real-time images can be stored in a data base memory cache (not shown in FIG. 1), from which they may be output to operator display 204 or a display 236 that is located elsewhere. Batch mode images or selected real time images are stored in a host database 238. When such images have been reconstructed and transferred to storage, the data processing server 214 notifies the data store server 216 on the operator workstation 116. The operator workstation 116 may be used by an operator to archive the images, produce films, or send the images via a network to other facilities.

The system, including the PET hardware described with respect to FIG. 2, may also include one or more networked workstations 242. By way of example, a networked workstation 242 may include a display 244; one or more input devices 246, such as a keyboard and mouse; and a processor 248. The networked workstation 242 may be located within the same facility as the operator workstation 102, or in a different facility, such as a different healthcare institution or clinic.

The networked workstation 242, whether within the same facility or in a different facility as the operator workstation 116, may gain remote access to the data processing server 214 or data store server 216 via the communication system 217. Accordingly, multiple networked workstations 242 may have access to the data processing server 214 and the data store server 216. In this manner, magnetic resonance data, reconstructed images, or other data may exchanged between the data processing server 214 or the data store server 216 or the storage and processing components of the PET hardware of FIG. 2 and the networked workstations 242, such that the data or images may be remotely prescribed, facilitated, accessed, or processed by a networked workstation 242. This data may be exchanged in any suitable format, such as in accordance with the transmission control protocol (TCP), the internet protocol (IP), or other known or suitable protocols.

Using a system such as described above with respect to FIGS. 1-3, the present disclosure provides improved time-of-flight (TOF) PET attenuation estimations, such as when using techniques such as described by M. Defrise, A. Rezaei, and J. Nuyts, "Time-of-flight PET data determine the attenuation sinogram up to a constant," Phys. Med. Biol., vol. 57, no. 4, pp. 885, 2012, which is incorporated herein by reference in its entirety, using a prior anatomical image. Specifically, as will be described, the present disclosure provides a maximum a posteriori (MAP) method to estimate an attenuation sinogram from TOF PET emission data and a co-registered anatomical image through a TOF data consistency condition and joint entropy based prior. The joint entropy between feature vectors extracted from the anatomical sinogram and attenuation sinogram can be used as a prior term in a Bayesian framework.

Figure 4:
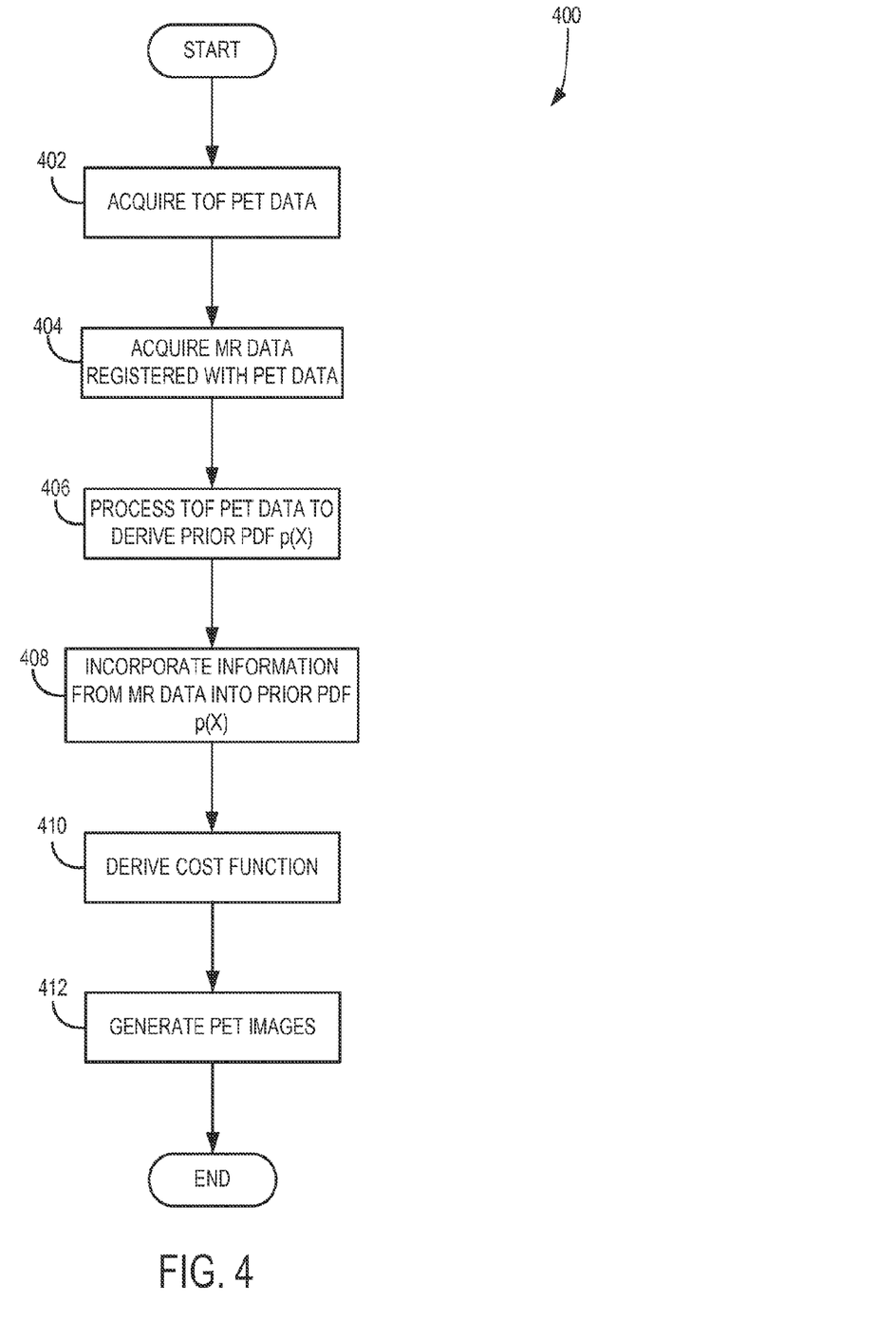
FIG. 4 is a flow chart setting forth exemplary steps of a method in accordance with the present invention.

Referring to FIG. 4, exemplary steps 400 of a process for improved TOF PET attenuation estimations using a prior anatomical image begins at process block 402 with the "acquisition" of TOF PET data. The "acquisition" may include gathering the data directly from the subject using a system, such as described above or may simply entail accessing previously-acquired TOF PET data. Likewise, MR image data co-registered with respect to the PET data is "acquired" at process block 404.

At process block 406, the PET data is processed to derive a prior probability density function (PDF). Specifically, the attenuated TOF PET data is denoted $m(s,\varphi,t)$, where $s$, $\varphi$, and $t$ are the transverse distance, projection angle, and TOF bin coordinate, respectively. The TOF PET data consistency condition is given by the partial differential equation:

$$t\partial m/\partial s + \partial m/\partial\varphi - s\partial m/\partial t + \sigma^2 \partial^2 m/\partial s\partial t = (-mt - \sigma^2 \partial m/\partial t)\partial x/\partial s - m\partial x/\partial \varphi \qquad (3);$$

where $x$ denotes the attenuation sonogram and $\sigma$ is the standard deviation of the TOF Gaussian kernel decided by the TOF timing resolution of the PET system. Slightly modifying the right-hand side of equation (3), provides:

$$t\partial m/\partial s + \partial m/\partial \varphi - s\partial m/\partial t + \sigma^2 \partial^2 m/\partial s\partial t = [(-mt - \sigma^2 \partial m/\partial t)\partial/\partial s - m\partial/\partial \varphi]x \qquad (4).$$

Through discretizing equation (4) and approximating derivatives with finite central difference method, a simpler linear equation can be obtained as follows:

$$B = (A_1 D_s + A_2 D_\varphi)X \qquad (5);$$

where:

$$B = (TD_s + D_\varphi - SD_t + \sigma^2 D_s D_t)M,$$

$$A_1 = -MT - \sigma^2 D_t M,$$

$$A_2 = -M \qquad (6);$$

and T, S, M, and X denote descretized versions of $t$, $s$, $m$, and $x$, respectively, while $D_s$, $D_\varphi$, and $D_t$ are the differential operators along corresponding directions. This indicates that attenuation sinogram could be iteratively reconstructed by minimizing a properly defined cost function based the equation (5).

Denoting $R = (A_1 D_s + A_2 D_\varphi)X - B$, the maximum a posteriori (MAP) estimate of attenuation sonogram X can be expressed as:

$$\hat{X}_{MAP} = \underset{X \geq 0}{\mathrm{argmax}} \frac{p(R|X)p(X)}{p(R)} \qquad (7)$$
$$= \underset{X \geq 0}{\mathrm{argmax}}\, p(R|X)p(X);$$

where $p(X)$ is the prior PDF of attenuation sonogram X, and $p(R|X)$ is the likelihood function given by noise distribution of R.

Note that noise distributions of $A_1$ and $B_1$ are complicated and difficult to be directly incorporated due to multiple differential operations on Poisson-distributed data M. Therefore, as a simplification, the noise of R as Gaussian distributed can be approximated and a least-square data fitting term in the log-likelihood function can be used. The resulting cost function is presented as:

$$\text{Cost} = \tfrac{1}{2}\|(A_1 D_s + A_2 D_\varphi)X - B\|_2^2 - \log p(X) \qquad (8).$$

Referring again to FIG. 4, at process block 408, the information in the co-registered MR image is incorporated into the prior PDF $p(X)$ through an information theoretic similarity metric $D(X,Y)$ between attenuation sinogram and MR information. Since attenuation reconstruction is primarily done in the sinogram domain, forward projection of the MR images into MR sinograms is performed, to define $D(X,Y)$ as an information similarity metric between the feature vectors extracted from attenuation sinogram X and MR sonogram Y, respectively. To keep the high-resolution anatomical information of a MR image, this step can use a well-modeled TOF projector program for a TOF PET scanner. The prior PDF $p(X)$ can then be defined as:

$$p(X) = \exp(\beta D(X,Y))/N \qquad (9);$$

where N denotes a constant normalization factor and $\beta$ is the hyper-parameter to control the balance of data fitting and prior information.

Now, at process block 410, a cost function can be rewritten as:

$$\text{Cost} + \tfrac{1}{2}\|(A_1 D_s + A_2 D_\varphi)X - B\|_2^2 - \beta D(X,Y) \qquad (10).$$

The information theoretic similarity metric $D(X,Y)$ described above can be defined as mutual information or joint entropy between feature vectors extracted from attenuation sinogram X and anatomical sinogram Y. As joint density priors can usually produce more robust reconstructions than mutual information priors, $D(X,Y)$ can be defined in terms of joint density between a set of feature vectors as:

$$D(X,Y) = -\Sigma_i H(X_i, Y_i) \qquad (11);$$

where $X_i$ and $Y_i$ are the i-th feature vectors extracted from X and Y, respectively.

The scale-space method serves as a major basis for extracting feature vectors and utilizing anatomical information as it emphasizes prominent boundaries, which are most likely to be correlated in both sinograms. This method generates a set of image features from the original image by blurring it with an increasing filter width, and so gradually wipes out details and underlines prominent boundaries as image scale increases. Since the feature vectors need to be updated in every iteration, for example, the defined features may be only three from both sonograms. By limiting the defined features, an optimization procedure that is not overly complex can be provided. Specifically, the sinogram itself, a moderate Gaussian-blurred sonogram, and Laplacian of blurred sinogram may be used. The sum of three similarity metrics from these feature vectors allows a moderate weight to be assigned to boundary information and to accelerate the convergence rate at the sinogram boundaries.

To compute the joint entropy, the marginal and joint probability density functions can be estimated using the Gaussian kernel based Parzen window method, such as described in S. Somayajula et al., "PET image reconstruction using information theoretic anatomical priors," IEEE Trans. Med. Imag., vol. 30, no. 3, pp. 537-549, 2011, which is incorporated herein in its entirety by reference. The gradient of joint density can be readily approximated using a fast Fourier-convolution based method likewise suggested in Somayajula et al. The non-convexity of joint entropy would not impede convergence of this method as long as the weight of its gradient is not very large compared to the gradient of data fitting term. Thus, the cost function in (10) can be efficiently minimized using a gradient-based optimization method. The gradient estimation and integration can be combined into a common step to formulate a data fitting term. That is, the TOF data consistency condition provides the ability to evaluate a gradient of an attenuation sinogram from TOF PET emission data and, at process block 412 yield improved PET images from the PET data.

Notice the computation of least-square gradient is much more expensive than that of joint entropy gradient and dominates the computational complexity of this method; however, such alternatives are likewise possible. Since $A_1$, $A_2$, and B can be pre-computed from TOF emission data before reconstruction and both $D_s$ and $D_\varphi$ may be sparse matrices, if the emission data size is $N_s N_\varphi N_t$, then for each iteration the complexity of gradient estimation is $O(N_s N_\varphi N_t)$.

Because the TOF-consistency-condition-based-estimation method determines the attenuation sinogram to a constant, a constant estimation step, such as image segmentation and classification, may be used after optimization to correct the constant offset. For example, the attenuation values in a small region of the sinogram may be given and can be applied to correct the sinogram range. In practice, this constant can be computed from an MR image.

Numerical Analysis and Results
Phantom and Simulated Data

Figure 5A:
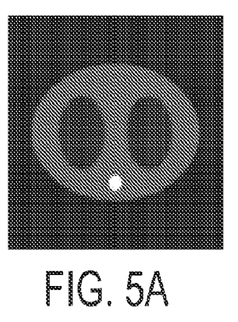
FIGS. 5A, 5B, and 5C are images of a phantom illustrating a true activity image, attenuation image, and MRI image, respectively.
Figure 5B:
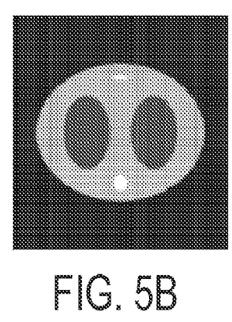
Figure 5C:
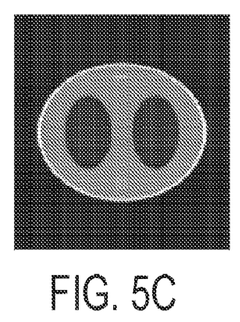

To evaluate the performance of this method though simulations on a 2D anthropomorphic phantom, the true activity image, attenuation image, and MRI image computed from the same phantom, all of size 256×256 and voxel size 0.11 cm, were considered, as illustrated in FIGS. 5A-5C. The attenuation coefficients are 0.032 cm$^{-1}$ for lung, 0.014 cm$^{-1}$ for bone and 0.096 cm$^{-1}$ for other tissues.

The 2D TOF emission sinogram was generated using a TOFPET forward projector based on Siddon's ray tracing algorithm. The 2D attenuation sinogram and MR sinogram were obtained using the same projector by disabling its TOF function. The radius of scanner ring is 20 cm. The TOF kernel is Gaussian with a spatial FWHM of 7.50 cm (500 ps). The numbers of detectors, rays per angle and TOF bins are 256, 64, and 127, respectively. The TOF data were interleaved into sinogram size 128×128×127 with the pixel size of 1.4° along $\varphi$, 0.3125 cm along s and 0.23 cm along t, and the attenuation data were interleaved into size 128× 128 with the same transverse pixel size. The minimum attenuation percentage is 16.12 percent. In the attenuated emission data, the average and highest photon counts are 0.59 and 2.46, respectively.

Before the estimation of attenuation sinogram, a TOF interval $[t_1, t_2]$ along t was carefully selected to cover the largest object diameter. A sinogram support was acquired by forward projecting the image support, and then further reduced by masking pixels with values below some threshold in any emission sinogram within $[t_1, t_2]$. The noiseless (or noisy) attenuated emission sinogram was smoothed by a Gaussian filter with, for example, 2 (or 7) pixels transversal full-width, half-maximum (FWHM) and 16 pixels TOF FWHM, and the value of σ was then approximated as $\sigma^2 = \sigma_{TOF} + (16\Delta t)^2$, where $\Delta t$ is the bin interval along t.

Simulation Results

The two-steps estimation method in Defrise et al. was used as a baseline method. The two derivatives $D_s X$ and $D_\varphi X$ were first estimated by performing a least-squares fitting in t within the interval $[t_1, t_2]$. For each derivative, the inaccurate estimations (with very large absolute values) around boundaries as well as their four nearest neighbors in the same s or $\varphi$ direction were filtered out using the maximum of the absolute values in the central region of the derivative sinogram as a threshold. The attenuation sinogram was then estimated by 2500 iterations of Landweber algorithm, as suggested by Derfrise et al., and offset-corrected using the given attenuation values in the pre-defined region. To solve our MAP method with anatomical prior, a conjugate gradient (CG) method was used to minimize the cost function. The initial X was estimated using the inverse of trimmed diagonal elements in the Hessian matrix, whose small values below a certain threshold are excluded. The penalty parameter β was 500 for noiseless case and 2500 for noisy case. Four iterations of steepest descent with a vanishing step-size were used to warm up the process, followed by 50 iterations of CG with a backtracking-Armijo line search. At each iteration, three features are extracted from updated sinogram with a Gaussian kernel of standard deviation 2.0 pixels and a 3*3 Laplacian kernel given by:

$$\begin{bmatrix} 0 & 1 & 0 \\ 1 & -4 & 1 \\ 0 & 1 & 0 \end{bmatrix},$$

which are then used to compute the gradient of joint entropy. The final sinogram is then adjusted with the given constant attenuation value.

Estimated results and their bias images were produced. The results demonstrated the direct MAP estimation using anatomic prior provided superior image quality, especially at the thin boundaries. Even for a very noisy data used in this simulation, a reasonable attenuation sinogram was still estimated. Also, the mean relative bias values and their standard deviations were computed in percentage in the whole sinogram, as well as four small regions of interest for each estimation result. In the noise-free case, the attenuation sinogram estimated by the MAP method yielded significantly (p<0.01) smaller bias (8.2±16.4 percent) in all regions as compared to the two-step method (−12.2±20.2 percent). In the presence of Poisson noise, the MAP estimation yielded accurate estimates of the attenuation sinogram (bias of 16.7±12.7 percent), while the analytical approach departed significantly from the true attenuation distributions (bias of 23.4±25.9 percent), p<0.01. Bias values and standard deviations in four regions of interest are listed in table 1 below.

TABLE 1

| Method | ROI 1 | ROI 2 | ROI 3 | ROI 4 |
|---|---|---|---|---|
| 2-step/ noise free | 6.81 ± 0.01 | −11.36 ± 0.00 | −20.51 ± 0.00 | 0.03 ± 0.05 |
| MAP/ noise-free | −1.66 ± 0.01 | 0.60 ± 0.00 | 3.26 ± 0.00 | −1.11 ± 0.00 |
| 2-step/ noisy | −19.73 ± 0.13 | −29.41 ± 0.05 | −32.14 ± 0.14 | −2.15 ± 0.14 |
| MAP/ noisy | −7.56 ± 0.11 | −2.17 ± 0.04 | −4.23 ± 0.14 | −0.18 ± 0.11 |

The major problem of both methods is incorrect estimation of left and right boundaries of the sinogram. Assigning a larger weight to the anatomical prior can reduce this error, but the convergence could be sacrificed due to the non-convexity of joint entropy. A spatially varying weight may be suitable to this situation, if necessary knowledge about boundary locations is given. Another problem is that certain kinds of areas in attenuation sinogram, such as the spine-related sine wave from left bottom to right top in the true attenuation sinogram, were missing in MR sinogram due to lower contrast of bone-tissue boundaries in regular MR imaging than in CT scan. In such cases, enforcing the maximization of similarity could not provide much help to the reconstruction.

Therefore, the present invention provides a MAP estimation method of PET attenuation with anatomical prior and PET data consistency condition. The method has been validated though idealized simulations on a thorax phantom with comparison to the original two-step method that does not utilize anatomical information. In both noise-free and noisy cases, the MAP method achieved superior estimation accuracy of the attenuation sinogram over other methods.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for correcting attenuation of positron emission tomography (PET) image data using magnetic resonance (MR) imaging data, the method comprising the steps of:
    a) acquiring PET sinogram data of a subject;
    b) acquiring MR image data of the subject that is registered with respect to the PET sinogram data;
    c) producing, using the PET sinogram data and MR image data, an estimate attenuation sinogram using a data consistency condition and joint entropy based prior by
        (i) deriving a prior probability density function (PDF) using the PET sinogram data,
        (ii) incorporating the MR image data into the prior PDF through an information theoretic similarity metric between the PET sinogram data and the MR image data by forward projecting the MR image data into MR sinogram data and defining the information theoretic similarity metric as feature vectors between the MR sinogram data and the PET sinogram data, and
        (iii) applying a joint entropy condition between the feature vectors extracted from the MR sinogram data and the PET sinogram data as a prior term in a Bayesian framework; and
    d) reconstructing a PET image using the estimated attenuation sinogram.

2. The method of claim 1 wherein the feature vectors are derived with respect to boundaries common to both the MR sinogram data and the PET sinogram data.

3. The method of claim 1 wherein step c) is performed by iteratively minimizing a cost function.

4. The method of claim 3 wherein the cost function is minimized using a gradient-based optimization method.

5. The method of claim 1 wherein the PET sinogram data is PET time-of-flight (TOF) data.

6. A system comprising:
    a non-transitive storage medium having stored thereon positron emission tomography (PET) sinogram data of a subject and magnetic resonance (MR) image data of the subject that is registered with respect to the PET sinogram data;
    a processor configured to:
    access the non-transitive storage medium;
    determine therefrom an estimate attenuation sinogram using a data consistency condition to evaluate a gradient of the PET sinogram data using the MR image data by
        i) deriving a prior probability density function (PDF) using the PET sinogram data,
        (ii) incorporating the MR image data into the prior PDF through an information theoretic similarity metric between the PET sinogram data and the MR image data by forward projecting the MR image data into MR sinogram data and defining the information theoretic similarity metric as feature vectors between the MR sinogram data and the PET sinogram data, and
        (iii) applying a joint entropy condition between the feature vectors extracted from the MR sinogram data and the PET sinogram data as a prior term in a Bayesian framework; and
    reconstruct an image of the subject using the estimate attenuation sinogram.

7. The system of claim 6 wherein the processor is further configured to minimize a cost function relating to the data consistency condition to reconstruct the image of the subject.

8. The system of claim 6 wherein the processor is further configured to derive the feature vectors with respect to boundaries common to both the MR sinogram data and the PET sinogram data.

9. The system of claim 6 wherein the processor is further configured to iteratively minimize a cost function to reconstruct the image of the subject.

10. The system of claim 9 wherein the processor is further configured to use a gradient-based optimization method to minimize the cost function.

11. The system of claim 6 further comprising a PET imaging system configured to acquire the PET sinogram data from the subject and an MR imaging system configured to acquire the MR image data from the subject.

12. The system of claim 11 wherein the PET imaging system and MR imaging system share a common bore.

13. A method for creating medical images of a subject using an estimation of attenuation corrections based on a time-of-flight (TOF) positron emission tomography (PET) data consistency condition, the method comprising the steps of:
- a) acquiring PET imaging data of a subject;
- b) acquiring non-PET imaging data of the subject;
- c) estimating, using the PET imaging data and the non-PET imaging data, an attenuation correction using a data consistency condition and joint entropy based prior by
  - (i) deriving a prior probability density function (PDF) using the PET imaging data,
  - (ii) incorporating the non-PET imaging data into the prior PDF through an information theoretic similarity metric between the PET imaging data and the non-PET imaging data by forward projecting the non-PET imaging data into non-PET sinogram data and defining the information theoretic similarity metric as feature vectors between the non-PET sinogram data and PET imaging data, and
  - (iii) applying a joint entropy condition between the feature vectors extracted from the non-PET sinogram data and the PET imaging data as a prior term in a Bayesian framework;
- d) correcting the PET imaging data based on step c) to create corrected PET imaging data; and
- e) reconstructing an image of the subject using the corrected PET imaging data.

* * * * *